US009655792B2

(12) United States Patent
Woo et al.

(10) Patent No.: US 9,655,792 B2
(45) Date of Patent: May 23, 2017

(54) ABSORBENT ARTICLE COMPRISING A MALODOR CONTROL COMPOSITION HAVING AN ACID CATALYST

(71) Applicant: The Procter & Gamble Company, Cincinnati, OH (US)

(72) Inventors: Ricky Ah-man Woo, Hamilton, OH (US); Steven Anthony Horenziak, Cincinnati, OH (US); Rhonda Jean Jackson, Cincinnati, OH (US); Zaiyou Liu, West Chester, OH (US); Michael-Vincent Nario Malanyaon, Indian Springs, OH (US); Jason John Olchovy, West Chester, OH (US); Christine Marie Readnour, Fort Mitchell, KY (US)

(73) Assignee: The Procter & Gamble Company, Cincinnati, OH (US)

( * ) Notice: Subject to any disclaimer, the term of this patent is extended or adjusted under 35 U.S.C. 154(b) by 403 days.

(21) Appl. No.: 14/169,816

(22) Filed: Jan. 31, 2014

(65) Prior Publication Data
US 2014/0186285 A1 Jul. 3, 2014

Related U.S. Application Data

(63) Continuation of application No. 12/970,098, filed on Dec. 16, 2010, now Pat. No. 8,674,167.
(Continued)

(51) Int. Cl.
*A61F 13/84* (2006.01)
*A61L 9/01* (2006.01)
(Continued)

(52) U.S. Cl.
CPC ............ *A61F 13/8405* (2013.01); *A61L 9/01* (2013.01); *A61L 9/014* (2013.01); *A61L 9/015* (2013.01);
(Continued)

(58) Field of Classification Search
CPC ............ A61F 13/8405; A61F 13/51113; A61F 2013/51076; A61F 2013/5109;
(Continued)

(56) References Cited

U.S. PATENT DOCUMENTS 5,382,567 A * 1/1995 Fuwa et al. ..................... 512/4
7,799,966 B2 9/2010 Williams et al.
(Continued)

FOREIGN PATENT DOCUMENTS

EP 1884251 2/2008
EP 1884251 A1 * 2/2008

OTHER PUBLICATIONS

PCT International Search Report, mail date Mar. 24, 2011, 5 pages.

*Primary Examiner* — Lynne Anderson
(74) *Attorney, Agent, or Firm* — Andres E. Velarde

(57) ABSTRACT

An absorbent article comprising a malodor control composition having at least one volatile aldehyde and an acid catalyst, and methods of use thereof, are provided. The malodor control composition is suitable for a variety of absorbent articles, including use in diapers, toddler training pants, adult incontinence garments, sanitary napkins, pantiliners, interlabial devices, hemorrhoid pads, and the like.

17 Claims, 1 Drawing Sheet

Related U.S. Application Data

(60) Provisional application No. 61/287,396, filed on Dec. 17, 2009.

(51) Int. Cl.
    *A61L 9/014*     (2006.01)
    *A61L 15/20*     (2006.01)
    *A61L 15/46*     (2006.01)
    *A61L 9/015*     (2006.01)
    *A61L 9/04*     (2006.01)
    *A61F 13/51*     (2006.01)

(52) U.S. Cl.
    CPC ............... *A61L 9/044* (2013.01); *A61L 15/20* (2013.01); *A61L 15/46* (2013.01); *A61F 2013/5109* (2013.01); *A61F 2013/51076* (2013.01); *A61F 2013/8408* (2013.01); *A61L 2209/21* (2013.01); *A61L 2300/21* (2013.01); *A61L 2300/216* (2013.01); *A61L 2300/45* (2013.01)

(58) Field of Classification Search
    CPC ...... A61F 2013/8408; A61F 2013/8411; A61F 2013/8435; A61L 15/46; A61L 9/01
    USPC .................................................. 604/359, 360
    See application file for complete search history.

(56) References Cited

U.S. PATENT DOCUMENTS

| | | |
|---|---|---|
| 2003/0158079 A1 | 8/2003 | Dykstra et al. |
| 2004/0082928 A1 | 4/2004 | Pesce et al. |
| 2005/0075617 A1 | 4/2005 | Vartiainen |
| 2007/0135319 A1* | 6/2007 | Wei et al. ............. 510/101 |
| 2008/0071238 A1 | 3/2008 | Sierri et al. |

* cited by examiner

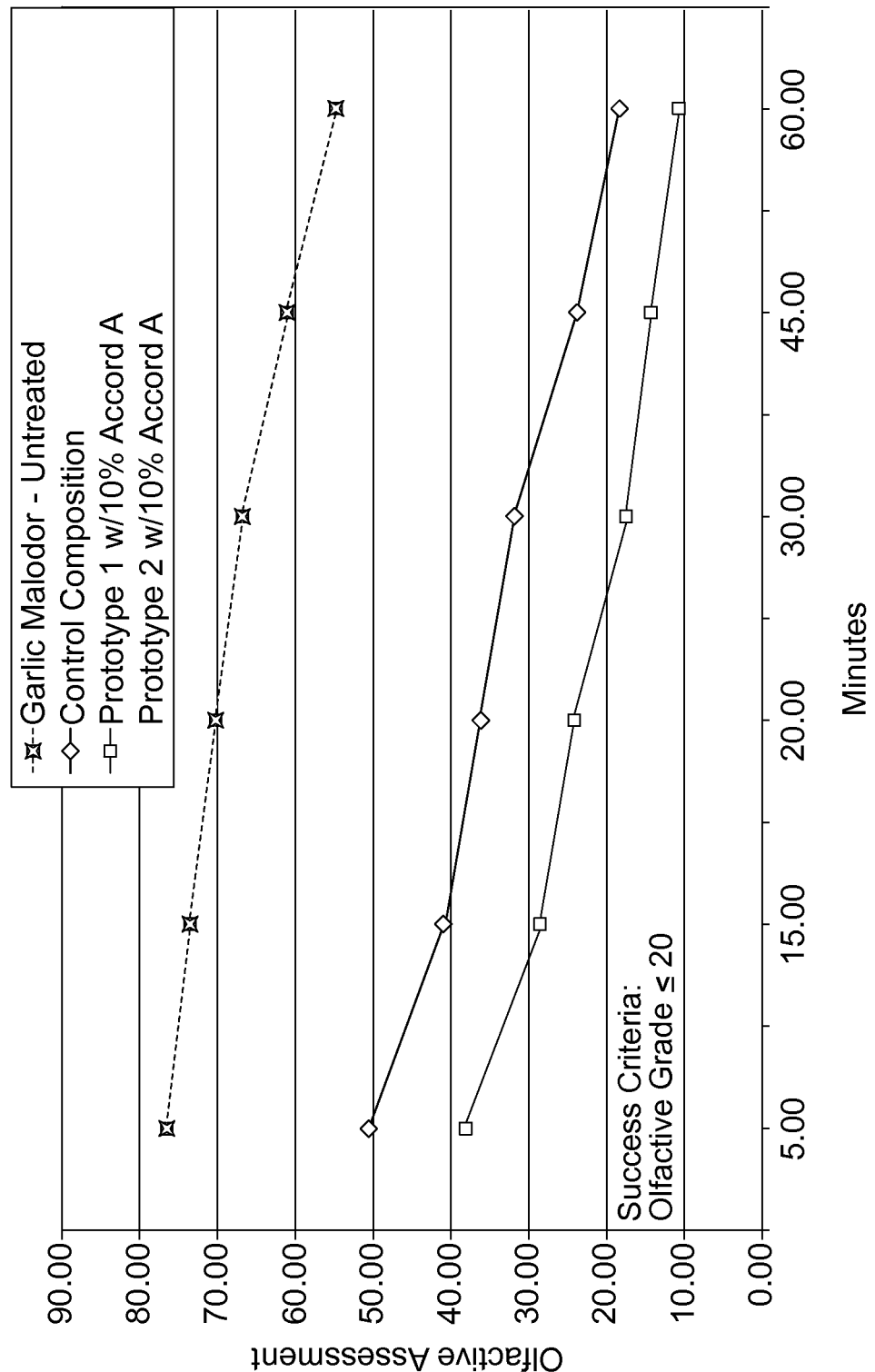

ABSORBENT ARTICLE COMPRISING A MALODOR CONTROL COMPOSITION HAVING AN ACID CATALYST

CROSS REFERENCE TO RELATED APPLICATION

This application claims the benefit of U.S. patent application Ser. No. 12/970,098, filed Dec. 16, 2010 which claims the benefit of U.S. Provisional Application No. 61/287,369, filed on Dec. 17, 2009; both incorporated herein by reference.

FIELD OF THE INVENTION

The present invention relates to an absorbent article comprising a malodor control composition having at least one volatile aldehyde and an acid catalyst, and methods of use. The malodor control composition is suitable for use in a variety of absorbent articles, including diapers, toddler training pants, adult incontinence garments, sanitary napkins, pantiliners, interlabial devices, hemorrhoid pads, and the like.

BACKGROUND OF THE INVENTION

Products for reducing or masking malodors are well known in the art and are widely described in patent literature. These products may be designed to work specifically in air or on fabrics or other surfaces. See, e.g., U.S. Pat. Nos. 5,942,217; 5,955,093; and 6,033,679. However, not all odors are effectively controlled by products on the market, such as amine-based malodors associated with urine and sulfur-based malodors associated with bodily fluids and excrements such as menses and feces, which are difficult to combat. Further, the time required for a composition to noticeably combat malodors may create consumer doubt as to a product's efficacy on malodors. For example, the malodor may become noticeable to a consumer of the product before the product begins to noticeably reduce the malodor.

In the context of absorbent articles, previous attempts have been made to develop compositions for incorporation in absorbent article to control malodor associated with bodily fluids and excrement, such as urine, menses, and feces. Some known malodor control compositions provide an overwhelming perfume scent to the product that may not be acceptable to some consumers. There thus still remains a desire to provide an improved malodor control composition for incorporation into an absorbent article product.

There remains a need for a fast acting malodor control composition that neutralizes malodors and is effective on a broad range of malodors, including amine-based and sulfur-based malodors, while not overpowering malodors with an overwhelming perfume.

SUMMARY OF THE INVENTION

The present invention encompasses an absorbent article comprising a malodor control composition comprising at least one volatile aldehyde; and an acid catalyst having a vapor pressure of about 0.01 to about 13 at 25° C.

The present invention further encompasses a method of neutralizing malodor comprising contacting the malodor with a malodor control composition comprising at least one volatile aldehyde; and an acid catalyst having a vapor pressure of about 0.01 to about 13 at 25° C.

BRIEF DESCRIPTION OF THE DRAWINGS

FIG. 1 is a graph showing butanethiol reduction by thiophene carboxaldehyde in combination with various acid catalysts.

DETAILED DESCRIPTION OF THE INVENTION

The present invention relates to a malodor control composition having at least one volatile aldehyde and an acid catalyst for neutralizing malodors, and methods thereof.

"Malodor" refers to compounds generally offensive or unpleasant to most people, such as the complex odors associated with bowel movements (i.e. feces) or other bodily excrements or fluids.

"Neutralize" or "neutralization" refers to the ability of a compound or product to reduce or eliminate malodorous compounds. Odor neutralization may be partial, affecting only some of the malodorous compounds in a given context, or affecting only part of a malodorous compound. A malodorous compound may be neutralized by chemical reaction resulting in a new chemical entity, by sequestration, by chelation, by association, or by any other interaction rendering the malodorous compound less malodorous or non-malodorous. Odor neutralization may be distinguished from odor masking or odor blocking by a change in the malodorous compound, as opposed to a change in the ability to perceive the malodor without any corresponding change in the condition of the malodorous compound.

"Absorbent article" refers to devices that absorb and contain body exudates, such as urine, menses, and feces. The term "disposable" is used herein to describe absorbent articles which are not intended to be laundered or otherwise restored or reused as an absorbent article after a single use. Examples of absorbent articles include diapers, toddler training pants, adult incontinence garments, and feminine hygiene garments such as sanitary napkins, pantiliners, interlabial devices, hemorrhoid pads, and the like.

Absorbent articles and components thereof, including the topsheet, backsheet, absorbent core, and any individual layers of these components, have a body surface and a garment surface. As used herein, "body surface" means that surface of the article or component which is intended to be worn toward or adjacent to the body of the wearer, while the "garment surface" is on the opposite side and is intended to be worn toward or placed adjacent to the wearer's undergarments when the disposable absorbent article is worn.

I. Absorbent Article

In general, the absorbent articles of the present invention typically comprise a topsheet, a backsheet, and an absorbent core disposed between the topsheet and backsheet.

The topsheet of the absorbent article is preferably compliant, soft feeling, and non-irritating to the wearers skin and hair. Further, the topsheet is liquid pervious, permitting liquids (e.g., menses and/or urine) to readily penetrate through its thickness. A suitable topsheet may be manufactured from a wide range of materials such as woven and nonwoven materials (e.g., a nonwoven web of fibers); polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. When the topsheet comprises a nonwoven web, the web may be manufactured by a wide number of known techniques. For example, the web may be spunbonded, carded, wet-laid, melt-blown, hydroentangled, combinations of the above, or the like.

The backsheet is impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contours of the human body. The backsheet prevents the exudates absorbed and contained in the absorbent core from wetting articles which contact the absorbent article such as bedsheets, pants, pajamas and undergarments. The backsheet can also be vapor permeable ("breathable"), while remaining fluid impermeable. The backsheet may comprise a woven or nonwoven material, polymeric films such as thermoplastic films of polyethylene or polypropylene, or composite materials such as a film-coated nonwoven material.

The backsheet and the topsheet can positioned adjacent the garment surface and the body surface, respectively, of the absorbent core. The absorbent core can be joined with the topsheet, the backsheet, or both in any manner as is known by attachment means such as those well known in the art. Embodiments of the present invention are envisioned wherein portions of the entire absorbent core are unattached to either the topsheet, the backsheet, or both.

The absorbent core can be formed from any of the materials well known to those of ordinary skill in the art. Examples of such materials include multiple plies of creped cellulose wadding, fluffed cellulose fibers, wood pulp fibers also known as airfelt, textile fibers, a blend of fibers, a mass or batt of fibers, airlaid webs of fibers, a web of polymeric fibers, and a blend of polymeric fibers.

For some absorbent articles, the absorbent core can be relatively thin, less than about 5 mm in thickness, or less than about 3 mm, or less than about 1 mm in thickness. Thickness can be determined by measuring the thickness at the midpoint along the longitudinal centerline of the pad by any means known in the art for doing while under a uniform pressure of 1.72 kPa. The absorbent core can comprise superabsorbent materials such as absorbent gelling materials (AGM), including AGM fibers, as is known in the art.

The absorbent article can comprise other additional components, for example between the topsheet and absorbent core, such as a secondary topsheet or acquisition layer. The secondary topsheet or acquisition layer can comprise a tissue layer or a nonwoven, such as carded resin-bonded nonwovens, embossed carded resin-bonded nonwovens, high-loft carded resin-bonded nonwovens, carded through-air-bonded nonwovens, carded thermo-bonded nonwovens, spun-bonded nonwovens, and the like. A variety of fibers can be used in the secondary topsheet or acquisition layer, including natural fibers, e.g. wood pulp, cotton, wool, and the like, as well as biodegradable fibers, such as polylactic acid fibers, and synthetic fibers such as polyolefins (e.g., polyethylene and polypropylene), polyesters, polyamides, synthetic cellulosics (e.g., RAYON®, Lyocell), cellulose acetate, bicomponent fibers, and blends thereof. The basis weight of the secondary topsheet or acquisition layer can vary depending upon the desired application.

The absorbent article can comprise further components such as side cuffs, typically found in diapers, or side wings or side flaps, typically found in sanitary napkins.

The absorbent articles herein are preferably disposable after a single use.

The malodor control composition of the present invention can be disposed in various locations in the absorbent article. The malodor control composition can be disposed on the garment-facing side or the body-facing side of the topsheet or absorbent core, or the body-facing side of the backsheet. Preferably, the malodor control composition is disposed on the absorbent core, and preferably on the garment-facing side of the absorbent core. The malodor control composition can also be disposed on other components, when present in the absorbent article, such as the garment-facing side or body-facing side of a secondary topsheet or acquisition layer.

II. Malodor Control Composition

The malodor control composition includes a mixture of volatile aldehydes and is designed to deliver genuine malodor neutralization and not function merely by covering up or masking odors. A genuine malodor neutralization provides a sensory and analytically measurable (e.g. gas chromatograph) malodor reduction. Thus, if the malodor control composition delivers a genuine malodor neutralization, the composition will reduce malodors in the vapor and/or liquid phase.

1. Volatile Aldehydes

The malodor control composition includes a mixture of volatile aldehydes that neutralize malodors in vapor and/or liquid phase via chemical reactions. Such volatile aldehydes are also called reactive aldehydes (RA). Volatile aldehydes may react with amine-based odors, following the path of Schiff-base formation. Volatiles aldehydes may also react with sulfur-based odors, forming thiol acetals, hemi thiolacetals, and thiol esters in vapor and/or liquid phase. It may be desirable for these vapor and/or liquid phase volatile aldehydes to have virtually no negative impact on the desired perfume character of a product. Aldehydes that are partially volatile may be considered a volatile aldehyde as used herein.

Suitable volatile aldehydes may have a vapor pressure (VP) in the range of about 0.0001 torr to 100 torr, alternatively about 0.0001 torr to about 10 torr, alternatively about 0.001 torr to about 50 torr, alternatively about 0.001 torr to about 20 torr, alternatively about 0.001 torr to about 0.100 torr, alternatively about 0.001 torr to 0.06 torr, alternatively about 0.001 torr to 0.03 torr, alternatively about 0.005 torr to about 20 torr, alternatively about 0.01 torr to about 20 torr, alternatively about 0.01 torr to about 15 torr, alternatively about 0.01 torr to about 10 torr, alternatively about 0.05 torr to about 10 torr, measured at 25° C.

The volatile aldehydes may also have a certain boiling point (B.P.) and octanol/water partition coefficient (P). The boiling point referred to herein is measured under normal standard pressure of 760 mmHg. The boiling points of many volatile aldehydes, at standard 760 mm Hg are given in, for example, "Perfume and Flavor Chemicals (Aroma Chemicals)," written and published by Steffen Arctander, 1969.

The octanol/water partition coefficient of a volatile aldehyde is the ratio between its equilibrium concentrations in octanol and in water. The partition coefficients of the volatile aldehydes used in the malodor control composition may be more conveniently given in the form of their logarithm to the base 10, logP. The logP values of many volatile aldehydes have been reported. See, e.g., the Pomona92 database, available from Daylight Chemical Information Systems, Inc.

(Daylight CIS), Irvine, Calif. However, the logP values are most conveniently calculated by the "CLOGP" program, also available from Daylight CIS. This program also lists experimental logP values when they are available in the Pomona92 database. The "calculated logP" (ClogP) is determined by the fragment approach of Hansch and Leo (cf., A. Leo, in Comprehensive Medicinal Chemistry, Vol. 4, C. Hansch, P. G. Sammens, J. B. Taylor and C. A. Ramsden, Eds., p. 295, Pergamon Press, 1990). The fragment approach is based on the chemical structure of each volatile aldehyde, and takes into account the numbers and types of atoms, the atom connectivity, and chemical bonding. The ClogP values, which are the most reliable and widely used estimates for this physicochemical property, are preferably used instead of the experimental logP values in the selection of volatile aldehydes for the malodor control composition.

The ClogP values may be defined by four groups and the volatile aldehydes may be selected from one or more of these groups. The first group comprises volatile aldehydes that have a B.P. of about 250° C. or less and ClogP of about 3 or less. The second group comprises volatile aldehydes that have a B.P. of 250° C. or less and ClogP of 3.0 or more. The third group comprises volatile aldehydes that have a B.P. of 250° C. or more and ClogP of 3.0 or less. The fourth group comprises volatile aldehydes that have a B.P. of 250° C. or more and ClogP of 3.0 or more. The malodor control composition may comprise any combination of volatile aldehydes from one or more of the ClogP groups.

In some embodiments, the malodor control composition of the present invention may comprise, by total weight of the malodor control composition, from about 0% to about 30% of volatile aldehydes from group 1, alternatively about 25%; and/or about 0% to about 10% of volatile aldehydes from group 2, alternatively about 10%; and/or from about 10% to about 30% of volatile aldehydes from group 3, alternatively about 30%; and/or from about 35% to about 60% of volatile aldehydes from group 4, alternatively about 35%.

Exemplary volatile aldehydes which may be used in a malodor control composition include, but are not limited to, Adoxal (2,6,10-Trimethyl-9-undecenal), Bourgeonal (4-t-butylbenzenepropionaldehyde), Lilestralis 33 (2-methyl-4-t-butylphenyl)propanal), Cinnamic aldehyde, cinnamaldehyde (phenyl propenal, 3-phenyl-2-propenal), Citral, Geranial, Neral (dimethyloctadienal, 3,7-dimethyl-2,6-octadien-1-al), Cyclal C (2,4-dimethyl-3-cyclohexen-1-carbaldehyde), Florhydral (3-(3-Isopropyl-phenyl)-butyraldehyde), Citronellal (3,7-dimethyl 6-octenal), Cymal, cyclamen aldehyde, Cyclosal, Lime aldehyde (Alpha-methyl-p-isopropyl phenyl propyl aldehyde), Methyl Nonyl Acetaldehyde, aldehyde C12 MNA (2-methyl-1-undecanal), Hydroxycitronellal, citronellal hydrate (7-hydroxy-3,7-dimethyl octan-1-al), Helional (alpha-methyl-3,4-(methylenedioxy)-hydrocinnamaldehyde, hydrocinnamaldehyde (3-phenylpropanal, 3-phenylpropionaldehyde), Intreleven aldehyde (undec-10-en-1-al), Ligustral, Trivertal (2,4-dimethyl-3-cyclohexene-1-carboxaldehyde), Jasmorange, satinaldehyde (2-methyl-3-tolylproionaldehyde, 4-dimethylbenzeneprop anal), Lyral (4-(4-hydroxy-4-methyl pentyl)-3-cyclohexene-1-carboxaldehyde), Melonal (2,6-Dimethyl-5-Heptenal), Methoxy Melonal (6-methoxy-2,6-dimethylheptanal), methoxycinnamaldehyde (trans-4-methoxycinnamaldehyde), Myrac aldehyde isohexenyl cyclohexenyl-carboxaldehyde, trifernal ((3-methyl-4-phenyl propanal, 3-phenyl butanal), lilial, P.T. Bucinal, lysmeral, benzenepropanal (4-tert-butyl-alpha-methyl-hydrocinnamaldehyde), Dupical, tricyclodecylidenebutanal (4-Tricyclo5210-2,6decylidene-8butanal), Melafleur (1,2,3, 4,5,6,7,8-octahydro-8,8-dimethyl-2-naphthaldehyde), Methyl Octyl Acetaldehyde, aldehyde C-11 MOA (2-methyl deca-1-al), Onicidal (2,6,10-trimethyl-5,9-undecadien-1-al), Citronellyl oxyacetaldehyde, Muguet aldehyde 50 (3,7-dimethyl-6-octenyl) oxyacetaldehyde), phenylacetaldehyde, Mefranal (3-methyl-5-phenyl pentanal), Triplal, Vertocitral dimethyl tetrahydrobenzene aldehyde (2,4-dimethyl-3-cyclohexene-1-carboxaldehyde), 2-phenylproprionaldehyde, Hydrotropaldehyde, Canthoxal, anisylpropanal 4-methoxy-alpha-methyl benzenepropanal (2-anisylidene propanal), Cylcemone A (1,2,3,4,5,6,7,8-octahydro-8,8-dimethyl-2-naphthaldehyde), and Precylcemone B (1-cyclohexene-1-carboxaldehyde).

Still other exemplary aldehydes include, but are not limited to, acetaldehyde (ethanal), pentanal, valeraldehyde, amylaldehyde, Scentenal (octahydro-5-methoxy-4,7-Methano-1H-indene-2-carboxaldehyde), propionaldehyde (propanal), Cyclocitral, beta-cyclocitral, (2,6,6-trimethyl-1-cyclohexene-1-acetaldehyde), Iso Cyclocitral (2,4,6-trimethyl-3-cyclohexene-1-carboxaldehyde), isobutyraldehyde, butyraldehyde, isovaleraldehyde (3-methyl butyraldehyde), methylbutyraldehyde (2-methyl butyraldehyde, 2-methyl butanal), Dihydrocitronellal (3,7-dimethyl octan-1-al), 2-Ethylbutyraldehyde, 3-Methyl-2-butenal, 2-Methylpentanal, 2-Methyl Valeraldehyde, Hexenal (2-hexenal, trans-2-hexenal), Heptanal, Octanal, Nonanal, Decanal, Lauric aldehyde, Tridecanal, 2-Dodecanal, Methylthiobutanal, Glutaraldehyde, Pentanedial, Glutaric aldehyde, Heptenal, cis or trans-Heptenal, Undecenal (2-, 10-), 2,4-octadienal, Nonenal (2-, 6-), Decenal (2-, 4-), 2,4-hexadienal, 2,4-Decadienal, 2,6-Nonadienal, Octenal, 2,6-dimethyl 5-heptenal, 2-isopropyl-5-methyl-2-hexenal, Trifernal, beta methyl Benzenepropanal, 2,6,6-Trimethyl-1-cyclohexene-1-acetaldehyde, phenyl Butenal (2-phenyl 2-butenal), 2.Methyl-3(p-isopropylphenyl)-propionaldehyde, 3-(p-isopropylphenyl)-propionaldehyde, p-Tolylacetaldehyde (4-methylphenylacetaldehyde), Anisaldehyde (p-methoxybenzene aldehyde), Benzaldehyde, Vernaldehyde (1-Methyl-4-(4-methylpentyl)-3-cyclohexenecarbaldehyde), Heliotropin (piperonal) 3,4-Methylene dioxy benzaldehyde, alpha-Amylcinnamic aldehyde, 2-pentyl-3-phenyl-propenoic aldehyde, Vanillin (4-methoxy 3-hydroxy benzaldehyde), Ethyl vanillin (3-ethoxy 4-hydroxybenzaldehyde), Hexyl Cinnamic aldehyde, Jasmonal H (alpha-n-hexyl-cinnamaldehyde), Floralozone, (para-ethyl-alpha,alpha-dimethyl Hydrocinnamaldehyde), Acalea (p-methyl-alpha-pentylcinnamaldehyde), methylcinnamaldehyde, alpha-Methylcinnamaldehyde (2-methyl 3-pheny propenal), alpha-hexylcinnamaldehyde (2-hexyl 3-phenyl propenal), Salicylaldehyde (2-hydroxy benzaldehyde), 4-ethyl benzaldehyde, Cuminaldehyde (4-isopropyl benzaldehyde), Ethoxybenzaldehyde, 2,4-dimethylbenzaldehyde, Veratraldehyde (3,4-dimethoxybenzaldehyde), Syringaldehyde (3,5-dimethoxy 4-hydroxybenzaldehyde), Catechaldehyde (3,4-dihydroxybenzaldehyde), Safranal (2,6,6-trimethyl-1,3-diene methanal), Myrtenal (pin-2-ene-1-carbaldehyde), Perillaldehyde L-4(1-methylethenyl)-1-cyclohexene-1-carboxaldehyde), 2,4-Dimethyl-3-cyclohexene carboxaldehyde, 2-Methyl-2-pentenal, 2-methylpentenal, pyruvaldehyde, formyl Tricyclodecan, Mandarin aldehyde, Cyclemax, Pino acetaldehyde, Corps Iris, Maceal, and Corps 4322.

In one embodiment, the malodor control composition includes a mixture of two or more volatile aldehydes selected from the group consisting of 2-ethoxy Benzylaldehyde, 2-isopropyl-5-methyl-2-hexenal, 5-methyl Furfural, 5-methyl-thiophene-carboxaldehyde, Adoxal, p-anisaldehyde, Benzylaldehyde, Bourgenal, Cinnamic aldehyde, Cymal, Decyl aldehyde, Floral super, Florhydral, Helional, Lauric aldehyde, Ligustral, Lyral, Melonal, o-anisaldehyde, Pino acetaldehyde, P.T. Bucinal, Thiophene carboxaldehyde, trans-4-Decenal, trans trans 2,4-Nonadienal, Undecyl aldehyde, and mixtures thereof.

In some embodiments, the malodor control composition includes fast reacting volatile aldehydes. "Fast reacting volatile aldehydes" refers to volatile aldehydes that either (1) reduce amine odors by 20% or more in less than 40 seconds; or (2) reduce thiol odors by 20% or more in less than 30 minutes.

In one embodiment, the malodor control composition includes a mixture of the volatile aldehydes listed in Table 1 and referred to herein as Accord A.

TABLE 1

Accord A

| Material | Wt. % | CAS Number | ClogP Group | VP(torr) @25° C. |
|---|---|---|---|---|
| Intreleven Aldehyde | 5.000 | 112-45-8 | 3 | 0.060 |
| Florhydral | 10.000 | 125109-85-5 | 4 | 0.008 |
| Floral Super | 25.000 | 71077-31-1 | 3 | 0.030 |
| Scentenal | 10.000 | 86803-90-9 | 2 | 0.010 |
| Cymal | 25.000 | 103-95-7 | 4 | 0.007 |
| o-anisaldehyde | 25.000 | 135-02-4 | 1 | 0.032 |

In another embodiment, the malodor control composition includes a mixture of the volatile aldehydes listed in Table 2 and referred to herein as Accord B.

TABLE 2

Accord B

| Material | Wt. % | CAS Number | ClogP Group | VP (torr) @25° C. |
|---|---|---|---|---|
| Intreleven Aldehyde | 2.000 | 112-45-8 | 3 | 0.060 |
| Florhydral | 20.000 | 125109-85-5 | 4 | 0.008 |
| Floral Super | 10.000 | 71077-31-1 | 3 | 0.030 |
| Scentenal | 5.000 | 86803-90-9 | 2 | 0.010 |
| Cymal | 25.000 | 103-95-7 | 4 | 0.007 |
| Floralozone | 10.000 | 67634-14-4 | 4 | 0.005 |
| Adoxal | 1.000 | 141-13-9 | 4 | 0.007 |
| Methyl Nonyl Acetaldehyde | 1.000 | 110-41-8 | 3 | 0.030 |
| Melonal | 1.000 | 106-72-9 | 3 | 0.670 |
| o-anisaldehyde | 25.000 | 135-02-4 | 1 | 0.032 |

In another embodiment, the malodor control composition includes a mixture of about 71.2% volatile aldehydes, the remainder being other an ester and an alcohol perfume raw material. This mixture is listed in Table 3 and referred to herein as Accord C.

TABLE 3

Accord C

| Material | Wt. % | CAS Number | ClogP Group | VP (torr) @25° C. |
|---|---|---|---|---|
| Intreleven Aldehyde | 2.000 | 112-45-8 | 3 | 0.060 |
| Florhydral | 10.000 | 125109-85-5 | 4 | 0.008 |
| Floral Super | 5.000 | 71077-31-1 | 3 | 0.030 |
| Scentenal | 2.000 | 86803-90-9 | 2 | 0.010 |
| Cymal | 15.000 | 103-95-7 | 4 | 0.007 |
| Floralozone | 12.000 | 67634-14-4 | 4 | 0.005 |
| Adoxal | 1.000 | 141-13-9 | 4 | 0.007 |
| Methyl Nonyl Acetaldehyde | 1.000 | 110-41-8 | 3 | 0.030 |

TABLE 3-continued

Accord C

| Material | Wt. % | CAS Number | ClogP Group | VP (torr) @25° C. |
|---|---|---|---|---|
| Melonal | 1.000 | 106-72-9 | 3 | 0.670 |
| Flor Acetate | 11.800 | 5413-60-5 | 1 | 0.060 |
| Frutene | 7.000 | 17511-60-3 | 4 | 0.020 |
| Helional | 5.000 | 1205-17-0 | 2 | 0.0005 |
| Bourgeonal | 2.000 | 18127-01-0 | 4 | 0.004 |
| Linalool | 10.000 | 78-70-6 | 3 | 0.050 |
| Benzaldehyde | 0.200 | 100-52-7 | 1 | 1.110 |
| o-anisaldehyde | 15.000 | 135-02-4 | 1 | 0.320 |

Accords A, B, or C can be formulated in with other perfume raw materials in an amount, for example, of about 10% by weight of the malodor control composition. Additionally, the individual volatile aldehydes or a various combination of the volatile aldehydes can be formulated into a malodor control composition. In certain embodiments, the volatile aldehydes may be present in an amount up to 100%, by weight of the malodor control composition, alternatively from about 0.1% to about 100%, alternatively from about 1% to about 100%, alternatively from about 2% to about 100%, alternatively from about 3% to about 100%, alternatively about 50% to about 100%, alternatively about 70% to about 100%, alternatively about 80% to about 100%, alternatively from about 1% to about 20%, alternatively from about 0.1% to about 10%, alternatively from about 1% to about 10%, alternatively from about 0.1% to about 5%, alternatively from about 1% to about 5%, alternatively from about 1% to about 3%, alternatively from about 2% to about 20%, alternatively from about 3% to about 20%, alternatively from about 4% to about 20%, alternatively from about 5% to about 20%, by weight of the composition.

In some embodiments where volatility is not important for neutralizing a malodor, the present invention may include poly-aldehydes, for example, di-, tri-, tetra-aldehydes. Such embodiments may include laundry detergents, additive, and the like for leave-on, through the wash, and rinse-off type of applications.

2. Acid Catalyst

The malodor control composition of the present invention may include an effective amount of an acid catalyst to neutralize sulfur-based malodors. It has been found that certain mild acids have an impact on aldehyde reactivity with thiols in the liquid and vapor phase. It has been found that the reaction between thiol and aldehyde is a catalytic reaction that follows the mechanism of hemiacetal and acetal formation path. When the present malodor control composition contains an acid catalyst and contacts a sulfur-based malodor, the volatile aldehyde reacts with thiol. This reaction may form a thiol acetal compound, thus, neutralizing the sulfur-based odor. Without an acid catalyst, only hemi-thiol acetal is formed.

Suitable acid catalysts have a VP, as reported by Scifinder, in the range of about 0.001 torr to about 38 torr, measured at 25° C., alternatively about 0.001 torr to about 14 torr, alternatively from about 0.001 to about 1, alternatively from about 0.001 to about 0.020, alternatively about 0.005 to about 0.020, alternatively about 0.010 to about 0.020.

The acid catalyst may be a weak acid. A weak acid is characterized by an acid dissociation constant, $K_a$, which is an equilibrium constant for the dissociation of a weak acid; the pKa being equal to minus the decimal logarithm of $K_a$. The acid catalyst may have a pKa from about 4.0 to about 6.0, alternatively from about 4.3 and 5.7, alternatively from about 4.5 to about 5, alternatively from about 4.7 to about 4.9. Suitable acid catalyst include those listed in Table 4.

TABLE 4

| Material | VP (torr) @ 25° C. |
| --- | --- |
| Formic Acid | 36.5 |
| Acetic Acid | 13.9 |
| Trimethyl Acetic Acid | 0.907 |
| Phenol (alkaline in liquid apps yet acidic in vapor phase) | 0.610 |
| Tiglic acid | 0.152 |
| Caprylic acid | 0.0222 |
| 5-Methyl thiophene carboxylic acid | 0.019 |
| Succinic acid | 0.0165 |
| Benzoic acid | 0.014 |
| Mesitylenic acid | 0.00211 |

Depending on the desired use of the malodor control composition, one may consider the scent character or the affect on the scent of the malodor control composition when selecting an acid catalyst. In some embodiments of the malodor control composition, it may be desirable to select an acid catalyst that provides a neutral to pleasant scent. Such acid catalysts may have a VP of about 0.001 torr to about 0.020 torr, measured at 25° C., alternatively about 0.005 torr to about 0.020 torr, alternatively about 0.010 torr to about 0.020 torr. Non-limiting examples of such acid catalyst include 5-methyl thiophene carboxaldehyde with carboxylic acid impurity, succinic acid, or benzoic acid.

The malodor control composition may include about 0.01% to about 5%, alternatively about 0.04% to about 1.5%, alternatively about 0.1% to about 1.0%, alternatively about 0.1% to about 0.5%, alternatively about 0.01% to about 0.4%, alternatively about 0.1% to about 0.4%, alternatively about 0.04% to about 1.5%, alternatively about 0.4% of an acid catalyst by weight of the malodor control composition.

In an acetic acid system, the present malodor control composition may include about 0.4% of acetic acid (50:50 TC:DPM, 0.4% acetic acid).

TABLE 5

| Sample Formulated | Actual % acetic acid in DPM | % Butanethiol reduction @ 30 min. |
| --- | --- | --- |
| 50:50 TC:DPM 0% Acetic Acid | 0.00 | 12.00 |
| 50:50 TC:DPM 0.05% Acetic Acid | 0.04 | 14.65 |
| 50:50 TC:DPM 0.1% Acetic Acid | 0.10 | 25.66 |
| 50:50 TC:DPM 0.2% Acetic Acid | 0.42 | 34.68 |
| 50:50 TC:DPM 0.5% Acetic Acid | 1.00 | 24.79 |
| 50:50 TC:DPM 1.0% Acetic Acid | 2.00 | 7.26 |

When an acid catalyst is present with a volatile aldehyde (or RA), the acid catalyst may increase the efficacy of the volatile aldehyde on malodors in comparison to the malodor efficacy of the volatile aldehyde on its own. For example, 1% volatile aldehyde and 1.5% benzoic acid provides malodor removal benefit equal to or better than 5% volatile aldehyde alone.

The malodor control composition may have a pH from about 3 to about 8, alternatively from about 4 to about 7, alternatively from about, alternatively from about 4 to about 6.

3. Optional Ingredients

The malodor control composition may, optionally, include odor masking agents, odor blocking agents, and/or diluents. For example, the malodor control composition may include a mixture of volatile aldehydes for neutralizing a malodor, perfume ionones, and a diluent. Alternatively, the malodor control composition may include 100% volatile aldehydes.

"Odor-masking agents" refer to known compounds (e.g. perfume raw materials) that mask or hide a malodorous compound. Odor-masking may include a compound with a non-offensive or pleasant smell that is dosed such it limits the ability to sense a malodorous compound. Odor-masking may involve the selection of compounds which coordinate with an anticipated malodor to change the perception of the overall scent provided by the combination of odorous compounds.

"Odor blocking agents" refer to known compounds that dull the human sense of smell.

Exemplary diluents include dipropylene glycol methyl ether, and 3-methoxy-3-methyl-1-butanol, and mixtures thereof.

The malodor control composition may also, optionally, include perfume raw materials that solely provide a hedonic benefit (i.e. that do not neutralize malodors yet provide a pleasant fragrance). Suitable perfumes are disclosed in U.S. Pat. No. 6,248,135, which is incorporated in its entirety by reference.

III. Method of Use

The malodor control composition of the present invention may be used in a wide variety of applications that neutralize malodors in the vapor and/or liquid phase. The malodor control composition may be formulated for use in substrates such as plastics, wovens, or non-wovens (e.g. cellulose fibers for paper products). Such substrates may be used as pet food packaging; paper towels; tissues; trash bags; diapers, toddler training pants; baby wipes; adult incontinence products; feminine hygiene products such as sanitary napkins and tampons.

In particular, the present invention encompasses a method of neutralizing malodor associated with urine, menses, and/or feces, comprising contacting said malodor with the absorbent article comprising the malodor control composition of the present invention. Examples of suitable absorbent articles include diapers, toddler training pants, adult incontinence garments, sanitary napkins, pantiliners, interlabial devices, hemorrhoid pads, and the like.

EXAMPLES

Analytical Test

Effect of Volatile Aldehydes on Amine-Based and Sulfur-Based Malodors

Malodor standards are prepared by pipeting 1 mL of butylamine (amine-based malodor) and butanethiol (sulfur-based malodor) into a 1.2 liter gas sampling bag. The bag is then filled to volume with nitrogen and allowed to sit for at least 12 hours to equilibrate.

A 1 µL sample of each volatile aldehyde listed in Table 6 and of each Accord (A, B, and C) listed in Tables 1 to 3 is pipeted into individual 10 mL silanized headspace vials. The vials are sealed and allowed to equilibrate for at least 12 hours. Repeat 4 times for each sample (2 for butylamine analysis and 2 for butanethiol analysis).

After the equilibration period, 1.5 mL of the target malodor standard is injected into each 10 mL vial. For thiol analysis, the vials containing a sample +malodor standard are held at room temperature for 30 minutes. Then, a 1 mL headspace syringe is then used to inject 250 µL of each sample/malodor into a GC/MS split/splitless inlet. For amine analysis, a 1 mL headspace syringe is used to inject 500 μL of each sample/malodor immediately into the GC/MS split/splitless inlet. A GC pillow is used for the amine analysis to shorten the run times.

Samples are then analyzed using a GC/MS with a DB-5, 20 m, 1 μm film thickness column with an MPS-2 autosampler equipment with static headspace function. Data is analyzed by ion extraction on each total ion current (56 for thiol and 30 for amine) and the area is used to calculate the percent reduction from the malodor standard for each sample.

Table 6 shows the effect of certain volatile aldehydes on neutralizing amine-based and sulfur based malodors at 40 seconds and 30 minutes, respectively.

TABLE 6

| Perfume Raw Material (R—CHO) | At least 20% butylamine reduction at 40 secs.? | At least 20% butanethiol reduction at 30 mins.? |
| --- | --- | --- |
| 2,4,5 Trimethoxy Benzaldehyde | No | No |
| 2,4,6-Trimethoxy-benzylaldehyde | No | No |
| 2-ethoxy benzylaldehyde | Yes | Yes |
| 2-isopropyl-5-methyl-2-hexenal | Yes | Yes |
| 2-methyl-3-(2-furyl)-propenal | No | No |
| 3,4,5 Trimethoxy Benzaldehyde | No | No |
| 3,4-Trimethoxy-benzylaldehyde | No | No |
| 4-tertbutyl benzylaldehyde | Yes | No |
| 5-methyl furfural | Yes | Yes |
| 5-methyl-thiophene-carboxaldehyde | No | Yes |
| Adoxal | Yes | No |
| Amyl cinnamic aldehyde | No | No |
| Benzylaldehyde | Yes | No |
| Bourgenal | No | Yes |
| Cinnamic aldehyde | Yes | Yes |
| Citronelyl Oxyacetaldehyde | No | No |
| Cymal | Yes | No |
| Decyl aldehyde | Yes | No |
| Floral Super | Yes | Yes |
| Florhydral | Yes | Yes |
| Floralozone | No | No |
| Helional | Yes | No |
| Hydroxycitronellal | No | No |
| Lauric aldehyde | Yes | No |
| Ligustral | Yes | No |
| Lyral | Yes | No |
| Melonal | Yes | No |
| Methyl nonyl acetaldehyde | No | No |
| o-anisaldehyde | Yes | Yes |
| p-anisaldehyde | Yes | No |
| Pino acetaldehyde | Yes | Yes |
| P.T. Bucinal | Yes | No |
| Thiophene Carboxaldehyde | Yes | No |
| Trans-4-decenal | Yes | Yes |
| Trans Trans 2,4-Nonadienal | Yes | No |
| Undecyl aldehyde | Yes | No |

Table 7 shows the percent reduction of butylamine and butanethiol at 40 seconds and 30 minutes, respectively, for Accords A, B, and C.

TABLE 7

| Accord | % reduction of butylamine at 40 secs. | % reduction of butanethiol at 30 mins. |
| --- | --- | --- |
| Accord A | 76.58 | 25.22 |
| Accord B | 51.54 | 35.38 |
| Accord C | 65.34 | 24.98 |

Analytical Test—Effect Of Acid Catalysts On Sulfur-Based Malodors

The above analytical test is repeated using samples containing an acid catalyst to test their effect on sulfur-based malodors. Specifically, a 1 μL aliquot of each of the following controls and acid catalyst samples are pipeted into individual 10 mL silanized headspace vials in duplicate: thiophene carboxyaldehyde as a control; a 50/50 mixture of thiophene carboxyaldehyde and each of the following acid catalysts at 0.04%, 0.10%, 0.43% in DPM, 1.02% in DPM, and 2.04% in DPM: phenol, mesitylenic acid, caprylic acid, succinic acid, pivalic acid, tiglic acid, and benzoic acid.

FIG. 1 demonstrates that low vapor pressure acid catalysts provide up to 3 times better reduction of sulfur-based malodors in comparison to the control.

Analytical Test—Effect Of Volatile Aldehydes And Acid Catalyst On Amine-Based And Sulfur-Based Malodors The above analytical test is repeated using sample formulations containing volatile aldehydes (or RA) and an acid catalyst, as outlined in Tables 8 and 9.

Tables 8 and 9 show that a perfume mixture having as little as 1% volatile aldehyde along with 1.5% acid catalyst performs better at reducing butylamine and butanethiol than the same perfume mixture having 5% volatile aldehyde.

TABLE 8

| Formulation | % butylamine reduction at 40 secs. | | % butanethiol reduction at 30 mins. | |
| --- | --- | --- | --- | --- |
| Perfume Mixture w/5% RA (Control) | 34.21 | — | 2.40 | — |
| Perfume Mixture w/1% RA and w/ 1.5% Benzoic Acid | 41.63 | +7.42 | 11.95 | +9.55 |
| Perfume Mixture w/3% RA and w/ 1.5% Benzoic Acid | 36.19 | +1.98 | 13.56 | +11.16 |
| Perfume A Mixture w/5% RA and w/ 1.5% Benzoic Acid | 41.26 | +7.05 | 9.56 | +5.02 |

TABLE 9

| Formulation | % butylamine Reduction at 40 secs. | | % butanethiol reduction at 30 mins. | |
| --- | --- | --- | --- | --- |
| Perfume mixture w/5% RA (Control) | 4.94 | — | 10.52 | — |
| Perfume mixture w/1% RA and w/ 1.5% Benzoic Acid | 11.61 | +6.67 | 18.82 | +8.30 |
| Perfume mixture w/3% RA and w/ 1.5% Benzoic Acid | 26.89 | +21.95 | 14.85 | +4.33 |
| Perfume mixture w/5% RA and w/ 1.5% Benzoic Acid | 20.27 | +15.33 | 16.84 | +6.32 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is, therefore, intended to cover in the appended claims all such changes and modifications that are within the scope of this invention.

What is claimed:

1. An absorbent article comprising a malodor control composition disposed therein, said malodor control composition comprising:
   at least one volatile aldehyde;
   an acid catalyst having a vapor pressure of about 0.01 to about 13 at 25° C.;
   wherein said at least one volatile aldehyde is present in an amount from about 0.1% to about 5%, by weight of said malodor control composition, and said acid catalyst is present in an amount of about 0.1% to about 1%, by weight of said malodor control composition.

2. The absorbent article of claim 1 wherein said at least one volatile aldehyde has a VP of about 0.001 to about 50 torr.

3. The absorbent article of claim 1 wherein said at least one volatile aldehyde has a VP of about 0.001 torr to about 15 torr.

4. The absorbent article of claim 1 wherein said at least one volatile aldehyde is selected from the group consisting of 2-ethoxy benzylaldehyde, 2-isopropyl-5-methyl-2-hexenal, 5-methyl furfural, 5-methyl-thiophene-carboxaldehyde, adoxal, p-anisaldehyde, benzylaldehyde, bourgenal, cinnamic aldehyde, cymal, decyl aldehyde, floral super, florhydral, helional, lauric aldehyde, ligustral, lyral, melonal, o-anisaldehyde, pino acetaldehyde, P.T. bucinal, thiophene carboxaldehyde, trans-4-decenal, trans trans 2,4-nonadienal, undecyl aldehyde, and mixtures thereof.

5. The absorbent article of claim 1 wherein said at least one volatile aldehyde is selected from the group consisting of flor super, o-anisaldehyde, and mixtures thereof.

6. The absorbent article of claim 1 wherein said at least one volatile aldehyde comprises a mixture of volatile aldehydes selected from the group consisting of Intreleven Aldehyde, Florhydral, 4,8.dimethyl-4,9.decadienal, Scentenal, Cymal, o-anisaldehyde, Floralozone, Adoxal, Methyl Nonyl Acetaldehyde, Melonal, Flor Acetate, Frutene, Helional, Bourgeonal, Linalool, Benzaldehyde, and mixtures thereof.

7. The absorbent article of claim 1 wherein said at least one volatile aldehyde comprises a mixture of volatile aldehydes, said mixture comprising about 0.1% to about 10% of Accord A, by weight of said malodor control composition; wherein Accord A comprises 5% by weight of Intreleven Aldehyde, 10% by weight of Florhydral, 25% by weight of 4,8.dimethyl-4,9.decadienal, 10% by weight of Scentenal, 25% by weight of Cymal, and 25% by weight o-anisaldehyde.

8. The absorbent article of claim 1 wherein said acid catalyst has a vapor pressure of about 0.01 to about 2 torr at 25° C.

9. The absorbent article of claim 1 wherein said acid catalyst is a carboxylic acid.

10. The absorbent article of claim 1 wherein said acid catalyst is present in an amount from about 0.01% to about 0.4%, by weight of said malodor control composition.

11. The absorbent article of claim 1 wherein said acid catalyst is present in an amount of about 0.4%, by weight of said malodor control composition.

12. The absorbent article of claim 1 wherein said composition has a pH of about 4 to about 6.5.

13. The absorbent article of claim 1 further comprising an ingredient selected from the group consisting of: odor masking agents, odor blocking agents, diluents, and mixtures thereof.

14. The absorbent article of claim 1, wherein said absorbent article is selected from the group consisting of a diaper, an adult incontinence garment, a sanitary napkin, a pantiliner, an interlabial device, and a hemorrhoid pad.

15. The absorbent article of claim 1, wherein said absorbent article further comprises a topsheet, a backsheet, and an absorbent core disposed between said topsheet and said backsheet.

16. The absorbent article of claim 15, wherein said absorbent core has a garment-facing side and a body-facing side, and wherein said malodor control composition is disposed on said garment-facing side of said absorbent core.

17. A method of neutralizing malodor associated with urine, menses, and/or feces, comprising contacting said malodor with the absorbent article of claim 1.

* * * * *